(12) United States Patent
Lees et al.

(10) Patent No.: US 6,302,843 B1
(45) Date of Patent: Oct. 16, 2001

(54) CENTRAL PLATFORM FOR SUPPORTING RETRACTOR BLADES AND THE LIKE DURING SURGERY

(75) Inventors: John Lees; Charles Warden, both of Richmond, VA (US)

(73) Assignee: Automated Medical Products Corporation, Sewaren, NJ (US)

( * ) Notice: Subject to any disclaimer, the term of this patent is extended or adjusted under 35 U.S.C. 154(b) by 0 days.

(21) Appl. No.: 09/513,829

(22) Filed: Feb. 25, 2000

Related U.S. Application Data
(60) Provisional application No. 60/124,997, filed on Mar. 18, 1999.

(51) Int. Cl.$^7$ ....................................................... A61B 1/32
(52) U.S. Cl. ............................ 600/228; 600/231; 600/234
(58) Field of Search ..................................... 600/227, 228, 600/229, 230, 231, 234

(56) References Cited

U.S. PATENT DOCUMENTS

| | | |
|---|---|---|
| 3,339,913 | 9/1967 | Anderson . |
| 4,099,521 | * 7/1978 | Nestor et al. ......................... 600/228 |
| 4,143,652 | 3/1979 | Meier et al. . |
| 4,254,763 | * 3/1981 | McCready et al. . |
| 4,461,284 | 7/1984 | Fackler . |
| 4,491,435 | 1/1985 | Meier . |
| 4,718,151 | * 1/1988 | LeVahn et al. ................... 600/230 X |
| 4,796,846 | 1/1989 | Meier et al. . |
| 4,945,897 | 8/1990 | Greenstein et al. . |
| 5,025,780 | * 6/1991 | Farley ................................. 600/230 |
| 5,162,039 | 11/1992 | Dahners . |
| 5,224,680 | 7/1993 | Greenstein et al. . |
| 5,365,921 | 11/1994 | Bookwalter et al. . |
| 5,441,042 | 8/1995 | Putman . |
| 5,529,571 | 6/1996 | Daniel . |
| 5,538,215 | 7/1996 | Hosey . |
| 5,662,300 | 9/1997 | Michelson . |
| 5,755,412 | 5/1998 | Guibert et al. . |
| 5,876,332 | 3/1999 | Looney . |
| 5,888,197 | * 3/1999 | Mulac et al. ......................... 600/234 |
| 5,899,627 | * 5/1999 | Dobrovolny ......................... 403/391 |
| 5,931,777 | 8/1999 | Sava . |
| 6,033,363 | * 3/2000 | Farley et al. ........................ 600/234 |

FOREIGN PATENT DOCUMENTS

| | | | |
|---|---|---|---|
| 1235135 | * 5/1960 | (FR) ..................................... 600/228 |
| WO 97/40752 | 11/1997 | (WO) . |

OTHER PUBLICATIONS

A.C. Stieber, *Hepatic Transplantation With the Aid of the Iron Intern Retractor*, The American Journal of Surgery, vol. 160, pp. 300–01, Sep. 1990.

R.J. Greenstein, *Mechanical Retraction in Obesity and Esophagogastric Surgery*, vol. 1, pp. 431–33, 1991.

* cited by examiner

*Primary Examiner*—Jeffrey A. Smith
(74) *Attorney, Agent, or Firm*—Blank Rome Comisky & McCauley LLP

(57) ABSTRACT

A central platform allows a hydra or other surgical device to be attached to a horizontal bar suspended over a patient during surgery. The platform is made of stainless steel and has integrally formed clamping and attaching portions. The clamping portion has a cylindrical bore for receiving the bar and a slot extending from the cylindrical bore. At least one thin portion adjacent the cylindrical bore allows the clamping portion to have enough flexibility for clamping. A key passes through a threaded bore and is tightened to clamp the clamping portion onto the bar. The attaching portion has a post for attaching the hydra or other device. The post has positioning projections to hold the hydra in a desired position. The post also has a threaded portion, so that the hydra can be held on with a wing nut.

15 Claims, 4 Drawing Sheets

CENTRAL PLATFORM FOR SUPPORTING RETRACTOR BLADES AND THE LIKE DURING SURGERY

REFERENCE TO RELATED APPLICATION

This application claims the benefit of U.S. Provisional Application No. 60/124,997, filed Mar. 18, 1999, whose disclosure is hereby incorporated by reference in its entirety into the present disclosure.

FIELD OF THE INVENTION

The present invention is directed to a central platform for supporting retractor blades and the like in a given position with respect to a patient during liver transplants and other similar surgical procedures and is more particularly directed to such a central platform for attachment to a horizontal bar suspended over the patient.

DESCRIPTION OF RELATED ART

It is known in the surgical arts to provide access to certain body parts during surgery by providing devices to hold certain other body parts out of the way. For example, during a liver transplant, it is often necessary to hold the rib cage up and the stomach out of the way; retaining devices having retaining blades at their ends can be attached to the above-mentioned horizontal bar to perform those functions. A well known example of that technology is the Stieber Rib Grip, sold by the assignee of the present application.

The Stieber Rib Grip 101 is shown in use in FIG. 1 and includes, inter alia, a horizontal bar 103 suspended over the patient P. Various clamping devices 105 are clamped to the horizontal bar 103 for holding retracting blades 107 that hold the patient P's stomach, rib cage, and the like out of the way.

Another example of known clamping devices used in surgical procedures and referred to as an Iron Intern® by the assignee herein is shown in FIGS. 2A–2C. FIG. 2A shows an assembly 201 assembled for use, FIG. 2B shows the assembly 201 in use on a patient P, and FIG. 2C shows various components of the assembly 201 disassembled for sterilization. The assembly 201 includes a swinger clamp 203 for attachment to a horizontal rail 205. The clamp 203 supports a rod 207 that includes a bend to define a vertical portion and a horizontal portion. On the top of the rod 207 is a securing mechanism 209 that engages with a multi-armed device 211, called a "hydra," by engagement with a hole 213 in a yoke 215 in the hydra 211. The yoke 215 supports jointed arms 217 having at their ends attachment portions 219 for holding retractor blades 221. FIG. 2B shows the hydra 211 used alongside a single-armed device 223.

Further details of the use of such devices and other related devices can be found in A. C. Stieber, "Hepatic Transplantation with the Aid of the Iron Intern Retractor," *The American Journal of Surgery*, Vol. 160, pp. 300–01, Sep., 1990; R. J. Greenstein, "Mechanical Retraction in Obesity and Esophagogastric Surgery," *Obesity Surgery*, Vol. 1, pp. 431–33, 1991; U.S. Pat. No. 56,224,680, issued to Greenstein et al on Jul. 6, 1993; U.S. Pat. No. 4,491,435, issued to Meier on Jan. 1, 1985; U.S. Pat. No. 4,143,652, issued to Meier et al on Mar. 13, 1979; and U.S. Pat. No. 4,796,846, issued to Meier et al on Jan. 10, 1989, whose disclosures are hereby incorporated by reference in their entireties into the present disclosure.

Heretofore, no satisfactory way has been found to incorporate the hydra 211 into the assembly 101 of FIG. 1. The conventional technique used by the assignee herein is to attach a C-clamp to the horizontal bar 103 and to attach the hydra 211 to the C-clamp. However, since the horizontal bar 103 normally used has a consistently circular cross-section, flattened portions are formed in the horizontal bar 103 to support the C-clamp to prevent unwanted rotation of the C-clamp and the attached hydra. Providing such flattened portions increases the cost of manufacture of the horizontal bar 103 and limits the angular orientations of the C-clamp to the angular orientations of the flattened portions.

SUMMARY OF THE INVENTION

It will be readily apparent from the above that a need exists in the art for a device for attachment to a horizontal bar having a circular cross-section for supporting a hydra or the like. Therefore, it is a primary object of the invention to provide a central platform having a portion for clamping onto such a horizontal bar and another portion for having a hydra or other similar equipment attached thereto.

It is another object of the invention to provide such a central platform that can be secured to such a horizontal bar without slipping and that can hold a hydra in a proper angular orientation.

It is still another object of the invention to provide such a central platform that can easily be sterilized.

To achieve the above and other objects, the present invention is directed to a central platform having a main body with a clamping portion and an attaching portion. The clamping portion has a cylindrical bore for receiving the horizontal bar and a slot extending from the bore to a surface of the clamping portion. The clamping portion can be formed from stainless steel and still have sufficient flexibility for clamping. The attaching portion has a post for receiving the hydra and projections for retaining the hydra in a desired angular orientation.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

Figure 3A:
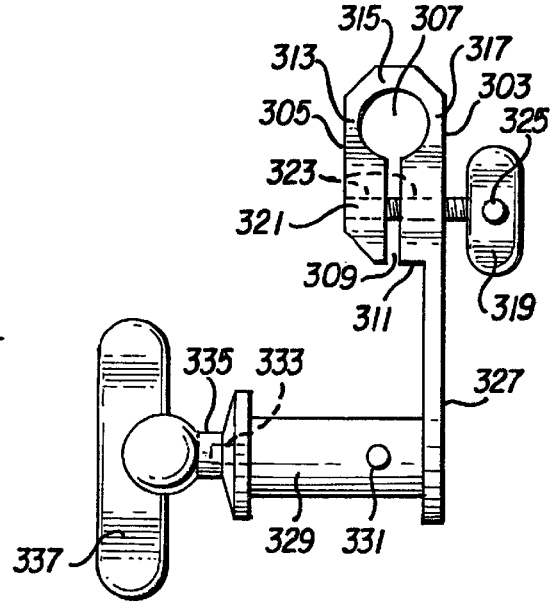
FIGS. 3A–3C show side, front, and back views, respectively, of a central platform according to the preferred embodiment.
Figure 3B:
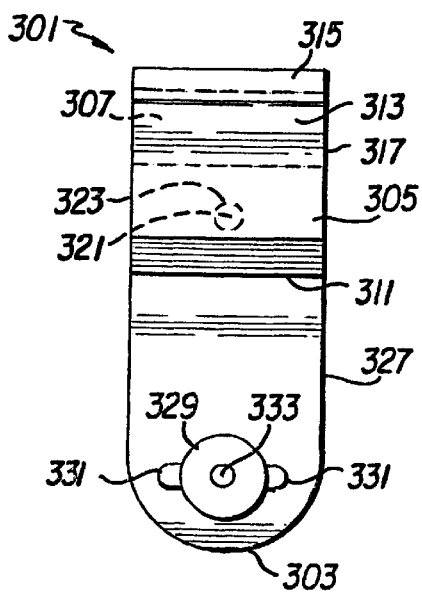

FIG. 3A shows a side view of the central platform 301 according to the preferred embodiment. FIG. 3B shows a front view of the central platform 301 with the wing nut 337 removed.

The central platform 301 is made of stainless steel and is formed on a main body 303. The main body 303 has an upper clamping portion 305 with a cylindrical bore 307 formed therein. A slot 309 connects the cylindrical bore 307 with a lower surface 311 of the upper clamping portion 305. The cylindrical bore 307 defines thin portions 313, 315, 317, at least one of which is thin enough to provide some flexibility for clamping, but all of which are strong enough to support whatever is attached to the central platform 301.

A key 319 has a threaded portion 321 engaged in a threaded bore 323 in the upper clamping portion 305. The upper clamping portion 305 can be tightened by turning the key 319, either by hand or by inserting an Allen wrench or other suitable tool into the hole 325.

The main body 303 also includes lower attaching portion 327 formed integrally with the upper clamping portion 305. The lower attaching portion holds an attaching post 329 having horizontal positioning projections 331 extending therefrom. The attaching post also has a threaded screw portion 333 engaging with a threaded bore 335 in a wing nut 337 that can be detached from the rest of the central platform 301 by unscrewing.

In use, the horizontal bar 103 is inserted through the cylindrical bore 307, and the upper clamping portion 305 is tightened on the horizontal bar 103 with the key 319. The hole 213 in the hydra 211 is engaged with the attaching post 329. The hole 213 has indentations around its edge for engaging the positioning projections 331 to secure the hydra 211 in a desired angular orientation. The wing nut 337 is screwed on to hold the hydra in place.

Figure 3C:
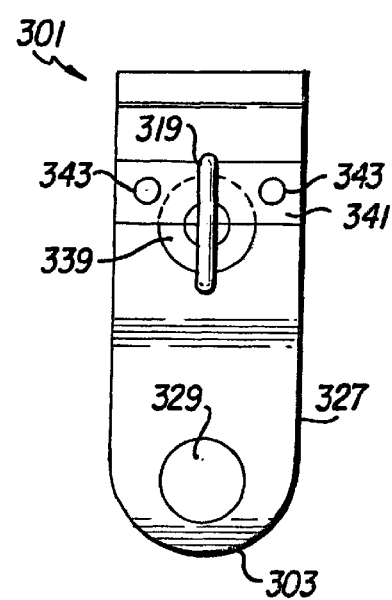

FIG. 3C shows a rear view of the central platform 301 with a provision for keeping the key 319 from being completely unscrewed. The key 319 has a wide portion 339 at the base of its threaded portion 321. The main body 303 has a plate 341 screwed on with screws 343 to cover the wide portion 339 at least partially and thus to retain the key 319.

Figure 1:
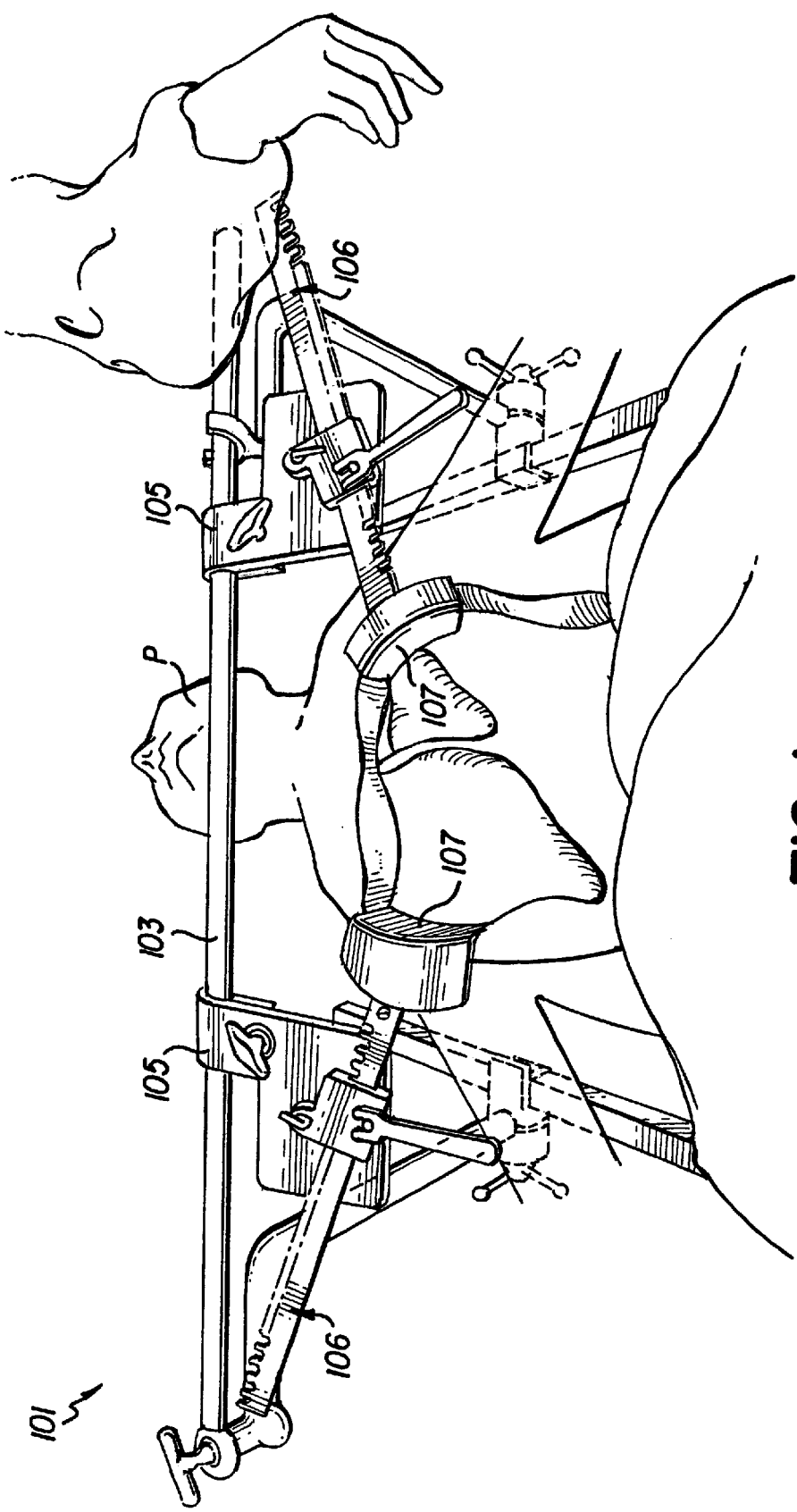
FIG. 1 shows one surgical assembly of the prior art.
Figure 2A:
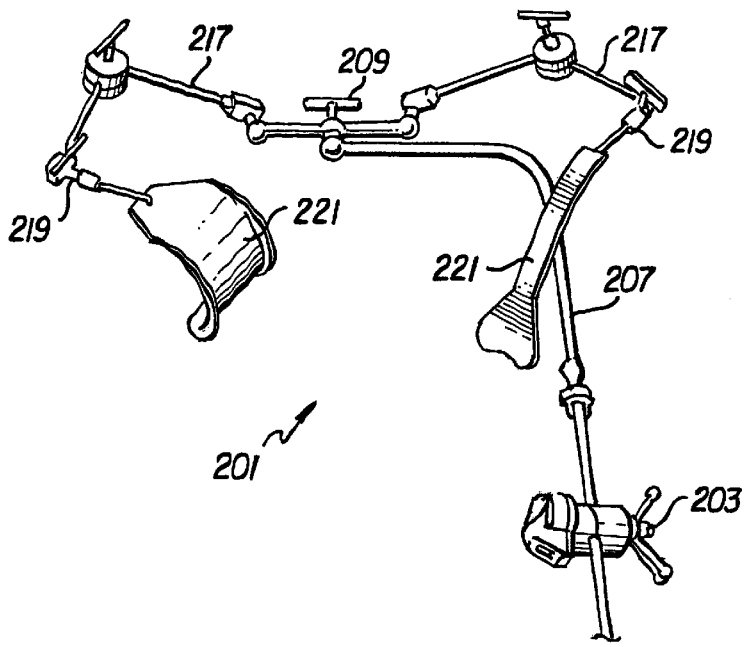
FIGS. 2A–2C show another surgical assembly of the prior art using a hydra.
Figure 2B:
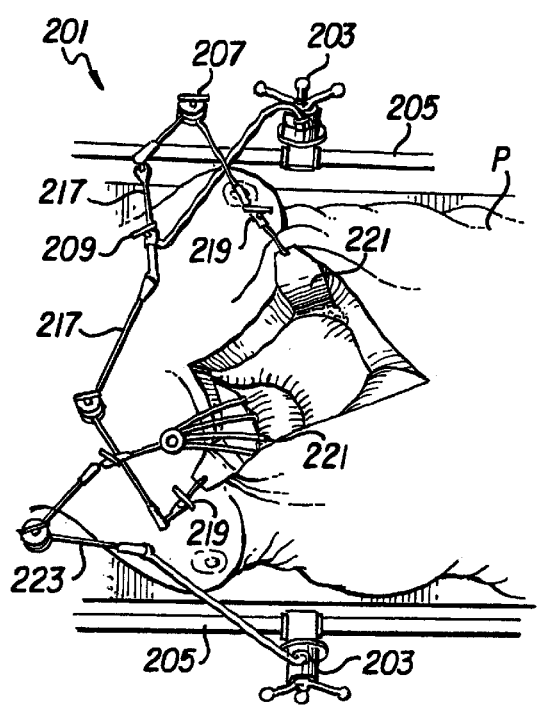
Figure 2C:
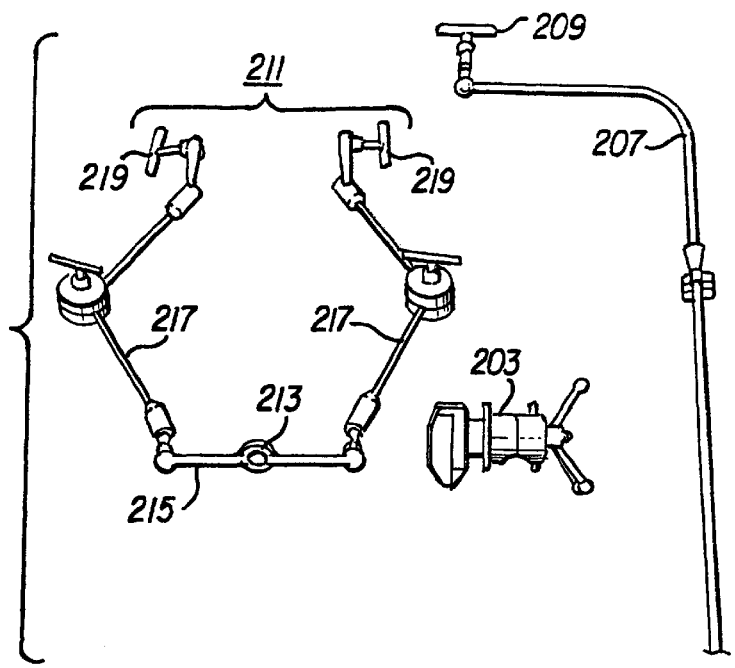
Figure 4:
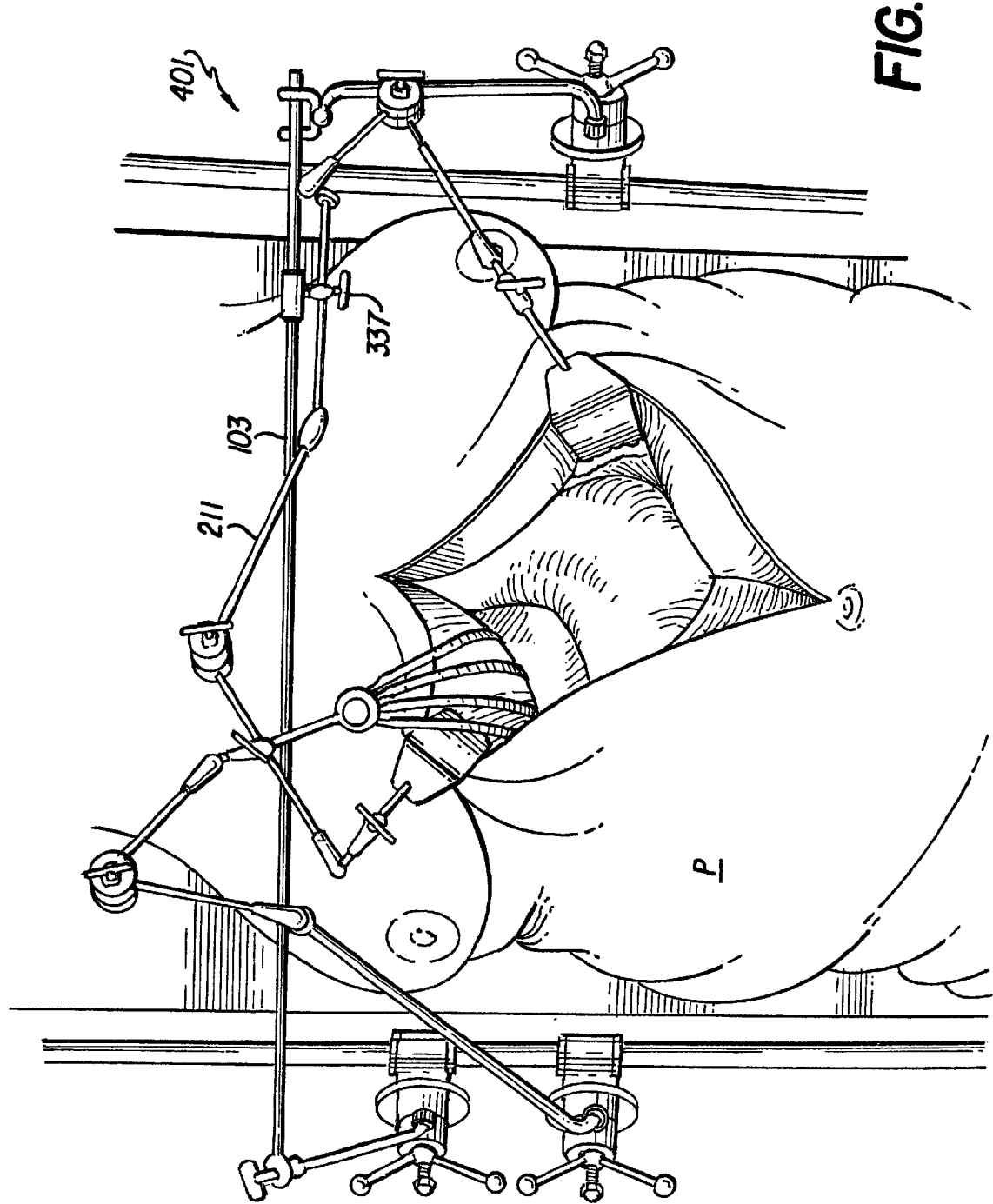
FIG. 4 shows the central platform of FIGS. 3A–3C used to incorporate the hydra of FIGS. 2A–2C into the surgical assembly of FIG. 1.

FIG. 4 shows an assembly 401 in which the central platform 301 is used to incorporate the hydra 211 of FIGS. 2A–2C into the Stieber Rib Grip 101 of FIG. 1. For purposes of clarity, however, the clamping devices 105, ratchet mechanism 106 and clamps 107 have been omitted. The horizontal bar 103 is suspended over the patient P in the known manner. The central platform 301 is clamped onto the horizontal bar 103 at a location determined in accordance with the surgical procedure to be performed. The hydra 211 is placed over the attaching post 329 (not shown in FIG. 4) and is held in place with the wing nut 337. The remaining components shown in FIG. 4 are the same as those shown in FIGS. 1 and 2A–2C. An additional swivel arm and implement may also be added, as shown.

While a preferred embodiment of the present invention has been set forth in detail, those skilled in the art who have reviewed the present disclosure will readily appreciate that other embodiments can be realized within the scope of the invention. For example, while a particular attachment for the hydra has been disclosed, any other attachment can be provided for attaching the hydra or any other desired device. Also, multiple attachments can be provided, e.g., one on each side of the main body. Moreover, the upper clamping portion and lower attaching portion can be formed separately and screwed together. Furthermore, the invention is not strictly limited to surgical applications. Therefore, the present invention should be construed as limited only by the appended claims.

What is claimed is:

1. A platform for attaching a device to a bar, the platform comprising:
   a clamping portion for being clamped onto the bar, the clamping portion having a bore formed therein for receiving the bar and a slot extending from the bore to an exterior surface of the clamping portion, the bore defining at least one thin portion adjacent to the bore for providing flexibility to the clamping portion to allow the slot to be expanded or contracted;
   a key engaged with the clamping portion for contracting the slot to clamp the clamping portion onto the bar; and
   an attaching portion, attached to the clamping portion, for receiving the device such that when the device is attached to the attaching portion and the clamping portion is clamped onto the bar, the device is attached to the bar through the attaching portion and the clamping portion;
   wherein the attaching portion comprises a post for being attached to the device.

2. The platform of claim 1, wherein the post comprises at least one positioning projection for engaging with the device to position the device relative to the platform.

3. The platform of claim 2, wherein the post further comprises a threaded portion for receiving a wing nut to secure the device to the post.

4. The platform of claim 1, wherein:
   the clamping portion has a threaded bore that intersects the slot; and
   the key comprises a threaded portion for engaging with the threaded bore.

5. The platform of claim 1, wherein the platform is formed of stainless steel.

6. The platform of claim 5, wherein the clamping portion and the attaching portion are integrally formed.

7. The platform of claim 1, wherein the clamping portion and the attaching portion are integrally formed.

8. A platform for attaching a device to a bar, the platform comprising:
   a clamping portion for being clamped onto the bar, the clamping portion having a bore formed therein for receiving the bar and a slot extending from the bore to an exterior surface of the clamping portion, the bore defining at least one thin portion adjacent to the bore for providing flexibility to the clamping portion to allow the slot to be expanded or contracted;
   a key engaged with the clamping portion for contracting the slot to clamp the clamping portion onto the bar; and
   an attaching portion, attached to the clamping portion, for receiving the device such that when the device is attached to the attaching portion and the clamping portion is clamped onto the bar, the device is attached to the bar through the attaching portion and the clamping portion; wherein:
   the clamping portion has a threaded bore that intersects the slot;
   the key comprises a threaded portion for engaging with the threaded bore; and
   the key further comprises a wide portion for preventing the key from being completely unscrewed from the clamping portion.

9. The platform of claim 8, wherein the platform is formed of stainless steel.

10. The platform of claim 9, wherein the clamping portion and the attaching portion are integrally formed.

11. The platform of claim 8, wherein the clamping portion and the attaching portion are integrally formed.

12. A platform for attaching a device to a bar, the platform comprising:
   a clamping portion for being clamped onto the bar, the clamping portion having a bore formed therein for receiving the bar and a slot extending from the bore to an exterior surface of the clamping portion, the bore defining at least one thin portion adjacent to the bore for providing flexibility to the clamping portion to allow the slot to be expanded or contracted;

a key engaged with the clamping portion for contracting the slot to clamp the clamping portion onto the bar; and an attaching portion, attached to the clamping portion, for receiving the device such that when the device is attached to the attaching portion and the clamping portion is clamped onto the bar, the device is attached to the bar through the attaching portion and the clamping portion;

wherein:

the clamping portion has a threaded bore that intersects the slot;

the key comprises a threaded portion for engaging with the threaded bore; and the key has a hole to permit the key to be turned by a tool inserted into the hole.

13. The platform of claim 12, wherein the platform is formed of stainless steel.

14. The platform of claim 13, wherein the clamping portion and the attaching portion are integrally formed.

15. The platform of claim 12, wherein the clamping portion and the attaching portion are integrally formed.

* * * * *